United States Patent

Allway

[11] Patent Number: 5,928,851
[45] Date of Patent: Jul. 27, 1999

[54] PHOTOGRAPHIC COUPLERS WHICH RELEASE USEFUL GROUPS ANCHIOMERICALLY AND THEIR SYNTHESIS

[75] Inventor: Philip Arthur Allway, Watford, United Kingdom

[73] Assignee: Eastman Kodak Company, Rochester, N.Y.

[21] Appl. No.: 08/864,089

[22] Filed: May 28, 1997

[30] Foreign Application Priority Data

Jun. 20, 1996 [GB] United Kingdom .................... 9612907

[51] Int. Cl.$^6$ ....................................................... G03C 1/73
[52] U.S. Cl. .......................... 430/549; 430/554; 430/555; 430/559
[58] Field of Search ..................................... 430/549, 554, 430/555, 559

[56] References Cited

U.S. PATENT DOCUMENTS

| | | | |
|---|---|---|---|
| 4,248,962 | 2/1981 | Lau .......................................... | 430/382 |
| 4,888,268 | 12/1989 | Itoh et al. ................................. | 430/561 |
| 5,091,293 | 2/1992 | Nozawa et al. .......................... | 430/555 |
| 5,096,804 | 3/1992 | Ikenoue et al. .......................... | 430/555 |
| 5,256,523 | 10/1993 | Sza .......................................... | 430/362 |
| 5,370,979 | 12/1994 | Kume ...................................... | 430/555 |
| 5,484,692 | 1/1996 | Mitsui et al. ............................. | 430/455 |
| 5,492,796 | 2/1996 | Ogiyama et al. ........................ | 430/543 |

FOREIGN PATENT DOCUMENTS

| 438129 | of 0000 | European Pat. Off. . |
|---|---|---|
| 57-56837 | 4/1982 | Japan . |
| 59-206834 | 11/1984 | Japan . |

*Primary Examiner*—Hoa Van Le
*Attorney, Agent, or Firm*—Sarah Meeks Roberts

[57] ABSTRACT

The present invention describes an image dye-forming coupler of formula (I)

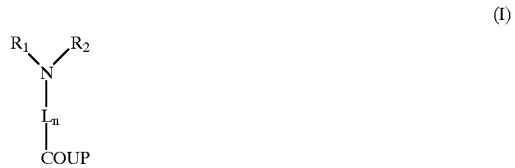

wherein L is an oxymethylene or oxycarbonyl group;
n is 0 or 1; COUP is a coupler moiety and $R_1$ and $R_2$ are the same or different and are groups selected such that (a) together with the nitrogen atom a good leaving group is formed;

(b) at least one of them contains a PUG linked to an electrophilic center (E); and (c) neither $R_1$ nor $R_2$ is a hydrogen atom wherein the coupler is a DIAR coupler from which inhibitor is released from a coupling-off group after a timed delay which results from an additional reaction step. Such delay permits control over the time of release, rate of release and rate of diffusion of a photographically useful group (PUG) without altering the nature of the PUG itself.

A method of preparing the coupler is also described wherein the two parts of the molecule can be built up separately and combined in a single reaction allowing ready access to a large variety of possible structures.

12 Claims, No Drawings

PHOTOGRAPHIC COUPLERS WHICH RELEASE USEFUL GROUPS ANCHIOMERICALLY AND THEIR SYNTHESIS

FIELD OF THE INVENTION

This invention relates to image dye-forming couplers, hereinafter called "couplers", for use in chromogenic development processes and to their method of synthesis. In particular the invention relates to couplers which release photographically useful groups, hereinafter called "PUGs", used in silver halide imaging systems where dyes are formed by oxidative coupling within the photographic layer, and in particular to magenta dye-forming couplers wherein the PUG is released after a delay, i.e. anchiomerically, and to photographic elements containing them

BACKGROUND OF THE INVENTION

Magenta couplers for use in commercial photographic materials, including films and papers, are usually drawn from the pyrazolone and pyrazolotriazole classes, in view of the stability of these compounds in raw-stock and their rapid and efficient reaction with oxidized color developers. Dyes derived from commercial pyrazolone and pyrazolotriazole magenta couplers also have acceptable spectrophotometric curve shapes. Magenta couplers are described in such representative patents and publications as: U.S. Pat. Nos. 2,311,082, 2,343,703, 2,369,489, 2,600,788, 2,908,573, 3,062,653, 3,152,896, 3,519,429, and "Farbkuppler-eine Literature-Ubersicht," published in Agfa Mitteilungen, Band III, pp. 126–156 (1961). Preferably such couplers are pyrazolones, pyrazolotriazoles, or pyrazolo-benzimidazoles.

It is also known to use image-modifying couplers which release development inhibitors on reaction with oxidized developer to provide one or more functions such as contrast or curve shape control, sharpness enhancement, granularity reduction and color correction via interlayer effects. The image-modifying couplers include development inhibitor releasing (DIR) couplers from which inhibitor is released directly as a coupling-off group.

Examples of DIR couplers are described in U.S. Pat. Nos. 3,137,578; 3,148,022; 3,148,062; 3,227,554; 3,384,657; 3,379,529; 3,615,506; 3,617,291; 3,620,746; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Colour Photography", C. R. Barr. J. R. Thirtle and P. W. Vittum in Photographic Science and Engineering, Vol. 13, p.174 (1969), incorporated herein by reference.

The image-modifying couplers also include development inhibitor anchiomerically releasing (DIAR) couplers from which inhibitor is released from a coupling-off group after a timed delay which results from an additional reaction step. This delay permits control over such parameters as time of release, rate of release and rate of diffusion of the PUG without altering the nature of the PUG itself.

Compounds having a nitrogen-linked coupling-off group which release PUGs after a delay are known from JP59-206834. The PUG is released by reaction of the electrophile (E) with the nucleophile (Nu) which is formed when A (coupler moiety) reacts with oxidized developer:

A-Nu-PUG-E

With compounds of this type, the PUG remains attached to the fragment of the Nu which was bonded to A. This makes it impossible to vary independently the PUG and the characteristics of the anchiomeric release mechanism.

U.S. Pat. No. 4,248,962 also describes the imagewise release of PUGS, from coupler compounds in photographic elements and processes, the couplers being represented by the structure:

COUP-TIME-PUG where COUP is a coupler moiety and TIME is a timing group, the coupler moiety being any moiety which will react with oxidized color developing agent to release the -TIME-PUG group. This patent is primarily concerned with couplers in which the nucleophile, Nu, attached to COUP, and the electrophile, E, attached to PUG, are spatially related by a linking group X, such as TIME=Nu-X-E. After displacement of Nu from COUP, an intramolecular nucleophilic displacement reaction occurs with the formation of a ring and release of the PUG.

Representative groups for Nu are listed and from the numerous examples it is clear that the linking atom to the COUP is in practice either a sulfur atom or preferably an oxygen atom. However there are problems associated with the use of aryloxy coupling-off groups attached to photographic couplers which give magenta dyes on reaction with oxidized developer. Thus the compounds are either unstable (e.g. aryloxypyrazolones) or difficult to make (e.g. aryloxypyrazolotriazoles). For compounds with an S-linking group, the intra-molecular reaction subsequent to reaction of the coupler with oxidized developer does not proceed satisfactorily.

Moreover the general method of synthesis described in the afore-mentioned patent, is sequential, i.e. all the molecule must be taken through each of a series of steps which leads to a cumbersome and lengthy process.

Problem to be Solved by Invention

There is therefore a need to provide compounds having an N-linking group which overcome the disadvantages associated with the aryloxy and arylmercapto compounds and to further provide a method for their preparation and in particular one in which the method is convergent, i.e. part of the molecule can be made using one sequence of reactions, the other part of the molecule can be made by using another sequence of reactions and then the two parts combined in a single reaction. This means that not all of the molecule has to go through each of the steps.

SUMMARY OF THE INVENTION

According to the present invention therefore there is provided an image dye-forming coupler of formula (I)

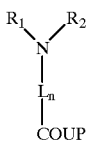

(I)

wherein L is an oxymethylene or oxycarbonyl group; n is 0 or 1; COUP is a coupler moiety and $R_1$ and $R_2$ are the same or different and are groups selected such that (a) together with the nitrogen atom a good leaving group is formed;

(b) at least one of them contains a PUG linked to an electrophilic center (E); and (c) neither $R_1$ nor $R_2$ is a hydrogen atom.

The present invention also includes a photographic element containing a compound of formula (I) as an image dye-forming coupler, in association with a light-sensitive silver halide emulsion layer.

In yet another aspect the present invention provides a multicolor photographic material comprising a support bearing yellow, magenta and cyan image dye-forming units comprising at least one blue-, green- or red-sensitive silver halide emulsion layer having associated therewith at least one yellow, magenta or cyan dye-forming coupler respectively, wherein at least one image dye-forming coupler is a coupler in accordance with the present invention.

There is further provided a method of synthesis of a compound of formula (I) which comprises when (i) $R_1$ and $R_2$ are different:
the reaction of a compound of formula (II)

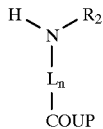

(II)

or (ii) when $R_1$ and R2 are the same:
the reaction of a compound of formula (IV)

(IV)

with a compound of formula (III)

LG-$R_1$ in the presence of a solvent,
wherein $R_1$, $R_2$, Ln and COUP are as hereinbefore defined and LG is a leaving group and at least $R_1$=X-E-PUG, wherein X is a linking group, E is an electrophilic center and PUG is a photographically useful group.

Advantageous Effect of the Invention

The compounds of the invention, which give magenta dyes with oxidized developer, are stable and easily prepared, unlike the aryloxy compounds. The compounds of the invention based on pyrazolones are more reactive than pyrazolones with a sulfur-linked coupling-off group as the latter have pKas which are too low for good activity. Furthermore both pyrazolones and pyrazolotriazoles with S-linked coupling-off groups suffer from the disadvantage that release of inhibitor from the coupling-off group is not satisfactory.

The characteristics of the anchiomeric release mechanism, such as the time over which it takes place, can be altered independently from those of the PUG. The fragment of the compound which performs the anchiomeric release becomes completely detached from the PUG. The compounds of the invention allow a wide variety of PUGs to be attached to a variety of photographic couplers.

Moreover the method of synthesis described herein is such that two parts of the complex molecules can be built up separately and combined in a single reaction, allowing ready access to a large variety of possible structures.

DETAILED DESCRIPTION OF THE INVENTION

Examples of $R_1$ and $R_2$ include but are not limited to alkyl, aryl, alkenyl, aralkyl, heterocyclyl; alkyl-, aryl- or heterocyclylsulfonyl; alkyl- or arylcarbonyl; alkyl- or arylthiocarbonyl; alkyl- or aryloxycarbonyl; alkyl- or arylthioalkoxycarbonyl; carbamoyl, thio-carbamoyl, imino or haloalkyl, each of which may be unsubstituted or substituted with any group that does not adversely affect the nature of the timing group or E, or $R_1$ and $R_2$ may, together with the nitrogen atom, form a 5–10 membered heterocyclic ring system which may contain one or more further heteroatoms selected from N, O and S, said ring being unsubstituted or substituted as hereindefined.

Preferably $R_1$ and $R_2$ are different and at least one is selected from unsubstituted or substituted alkyl-, aryl- or heteroarylsulfonyl; aryl or heteroaryl; and alkyl- and arylcarbonyl; most preferably arylsulfonyl.

Unless otherwise specifically stated, substituent groups usable on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N- dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

As used herein and throughout the specification the term alkyl refers to an unsaturated or saturated straight chain or branched chain alkyl group having 1–20 atoms and includes cycloalkyl having 3–8 carbon atoms.

Examples of electrophilic centers (E) to which a PUG can be attached include, but are not limited to, unsubstituted or substituted primary, secondary or tertiary alkyl; alkyl- or arylcarbonyl; alkyl- or arylimino; thiocarbonyl; alkyl- or aryloxycarbonyl, alkyl- or arylthioalkoxycarbonyl; carbamoyl, thiocarbamoyl, alkenyl, phosphinyl or thiophosphinyl. The alkyl groups may or may not be next to another group such as aryl, carbonyl or thiocarbonyl.

Preferred (E)s are unsubstituted or substituted primary or secondary alkyl; alkyl- or arylcarbonyl; arylimino; alkyl- or aryloxycarbonyl or most preferably carbamoyl.

Photographically useful coupling-off groups (PUGs) are well-known in the art. Such groups can determine the equivalency of the coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, development acceleration or inhibition, bleach acceleration or inhibition, electron transfer facilitation and color correction.

Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptoooxazoles, mercaptothiadiazoles, mercaptothiazoles, mercaptotriazoles, mercaptothiatriazoles, mercaptooxadiazoles, mercaptodiazoles, mercaptooxathiazoles, tellurotetrazoles or benzisodiazoles.

The preferred bleach accelerator is mercaptopropionic acid.

In the compound of formula (I) n is preferably 0.

A suitable definition of a leaving group may be found in any standard organic textbook such as in, for example, J. March Advanced Organic Chemistry; Reactions, Mechanisms and Structure 4th Ed. p.205, Wiley Interscience, 1992.

The reaction between the compound of formula (II) or (IV) with (III) takes place in the presence of a solvent, preferably an aprotic solvent, such as acetonitrile, sulpholane, dimethylformamide, dimethylacetamide, dimethylsulfoxide, toluene, dichloromethane, pyridine or preferably tetrahydrofuran. Either an organic or an inorganic base may be used but organic bases are preferred and in particular tertiary amines such as triethylamine, diisopropylethylamine and dimethylaniline; tetramethylguanidine or most preferably pyridine. The reaction can be carried out at temperatures ranging from −20 C to 100 C, but most preferably and conveniently at 20 C (room temperature).

The compound of formula (II) or (IV) may in turn be readily prepared by methods known in the art for preparing amines. The compounds of formula (III) may suitably be prepared either (i) by conversion of a group attached to X into a leaving group LG

GROUP-X-E-PUG→LG-X-E-PUG or (ii) by a displacement reaction of a group attached to E by PUG

LG-X-E-GROUP+PUG→LG-X-E-PUG

The starting materials for these reactions are prepared according to methods known in the art.

Suitable leaving groups (LG) include halogen or unsubstituted or substituted alkyl- or arylthio; alkyl- or aryloxy; alkyl- or arylcarbonyloxy or amino, but preferably halogen.

The nature of the linking group (X) is such that Nu is spatially related with regard to E so that intra-molecular reaction can occur.

Examples of DIAR couplers which may be suitable for practicing the present invention include the following but the invention is in no way limited thereto:

Coupler 1

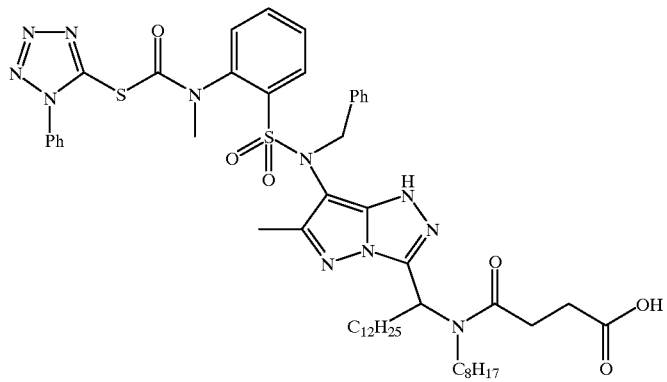

Coupler 2

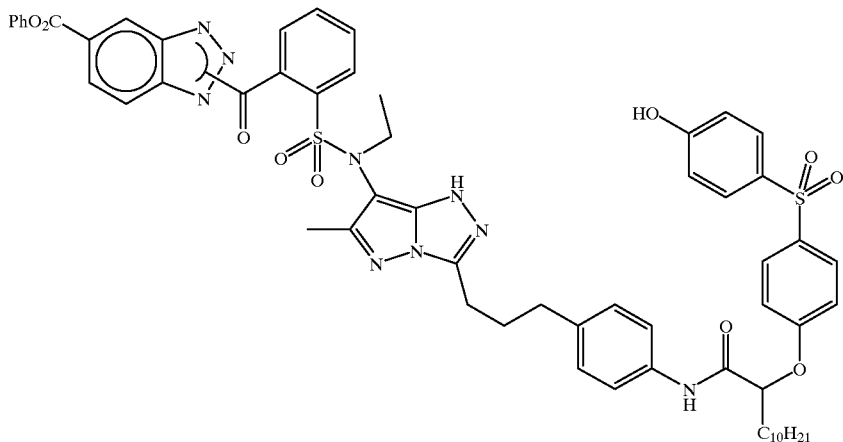

Coupler 3

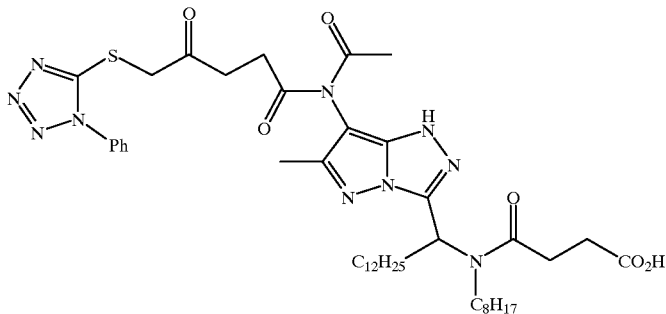

-continued
Coupler 4
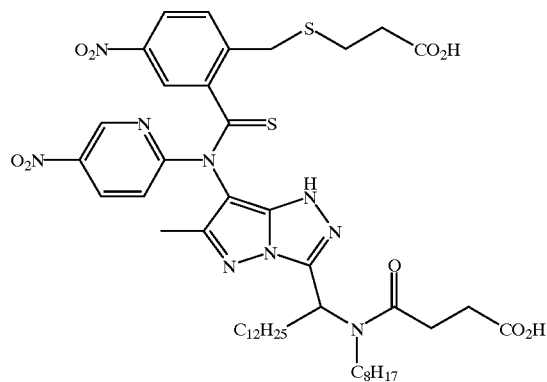
Coupler 5
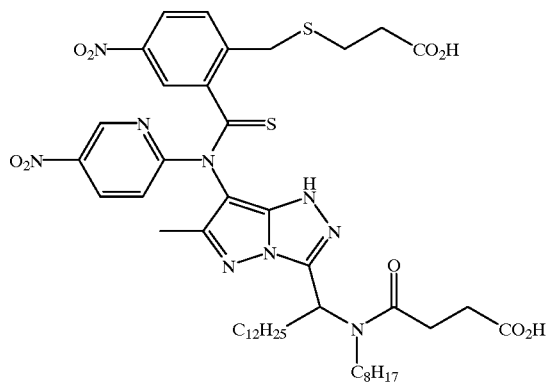
Coupler 6
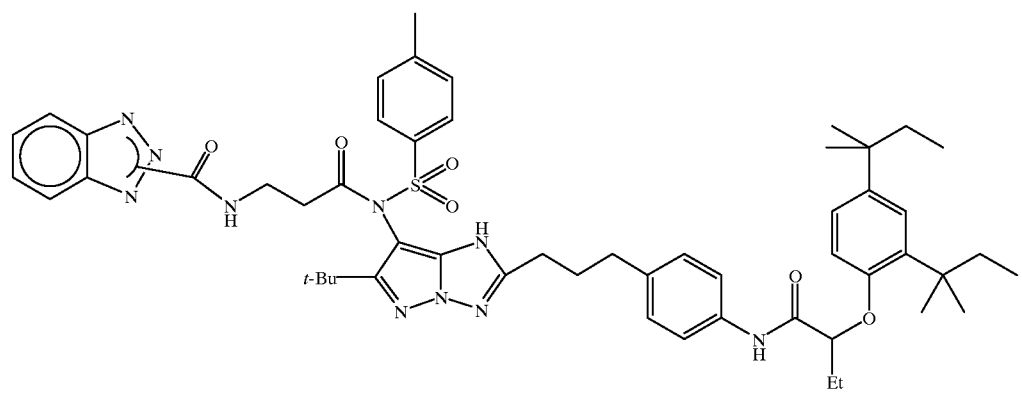
Coupler 7
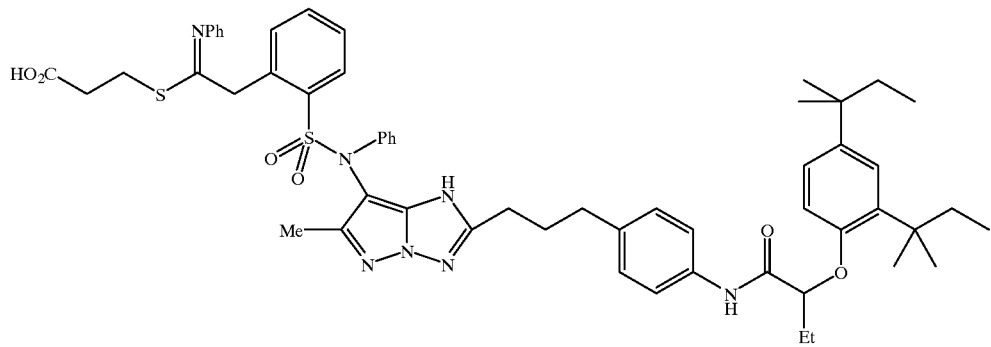

-continued
Coupler 8
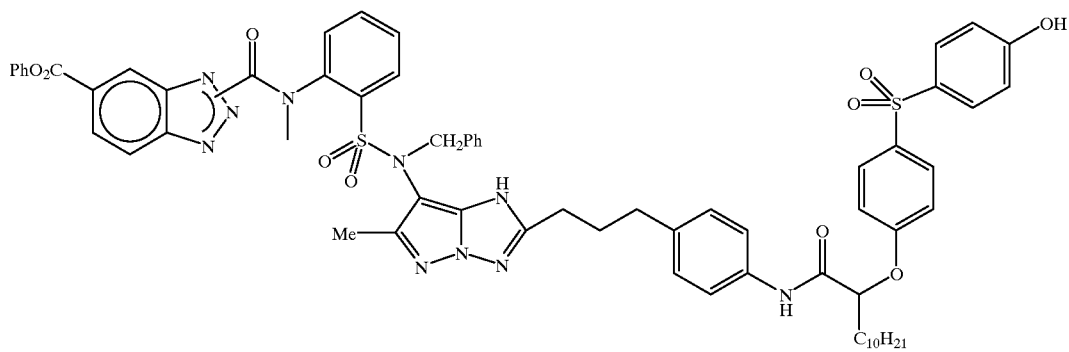
Coupler 9
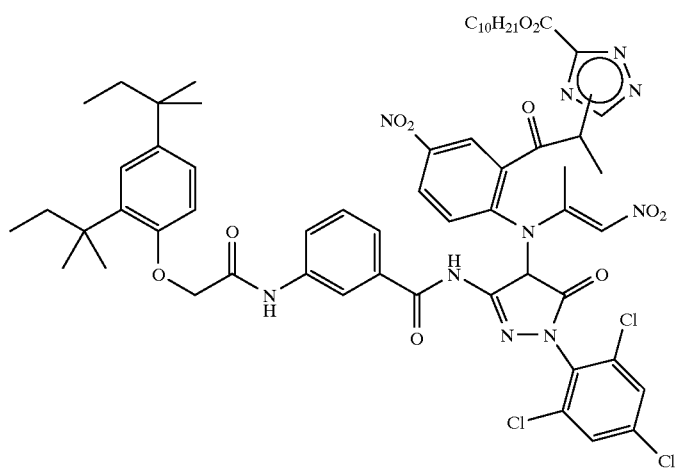
Coupler 10
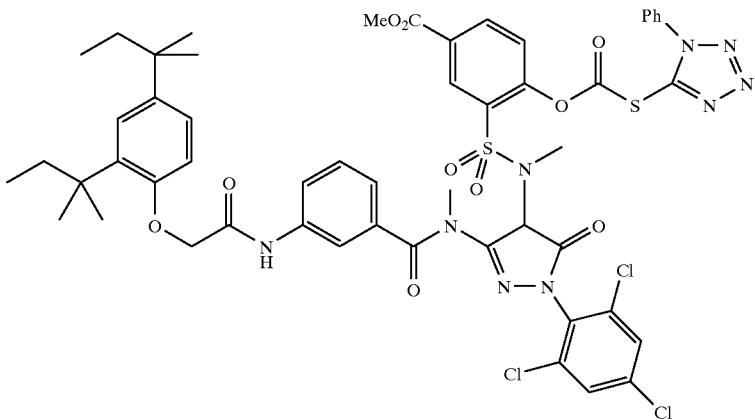

Coupler 11
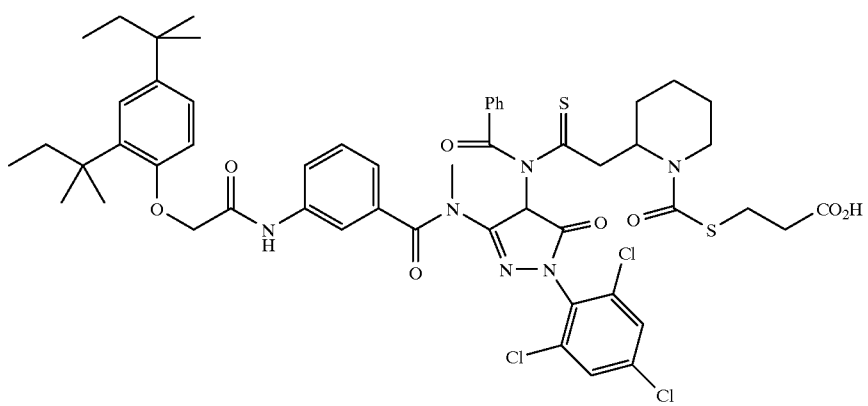
Coupler 12
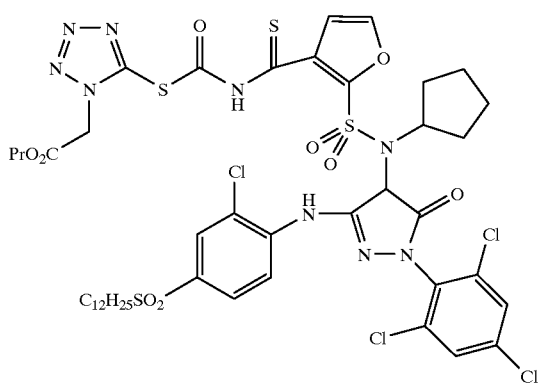
Coupler 13
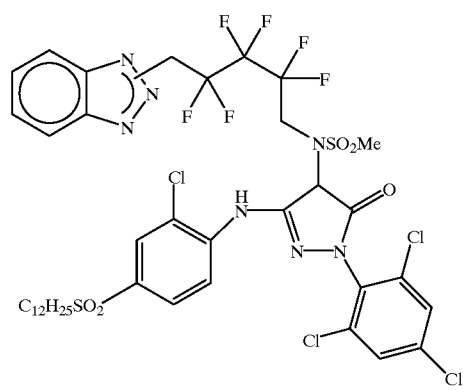

Coupler 14

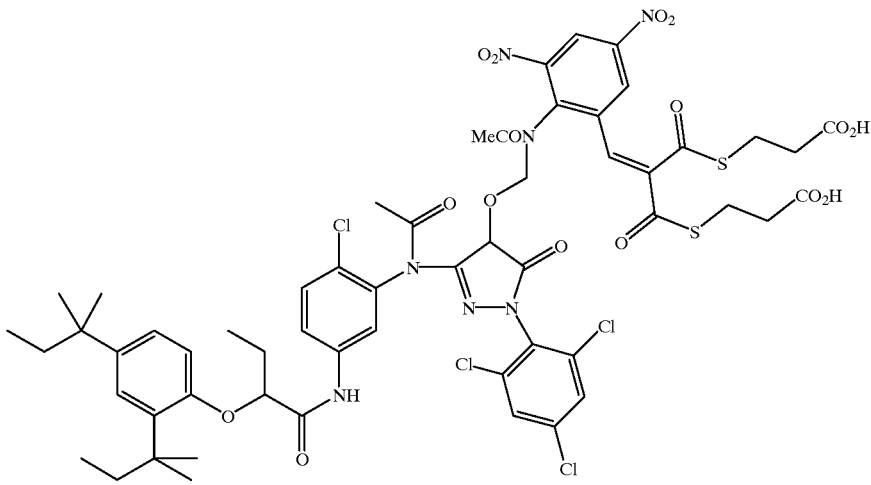

The photographic materials of the present invention may be simple elements or multilayer, multicolor elements. Multicolor elements contain image-dye-forming units sensitive to each of the three primary regions of the visible range of the electromagnetic spectrum. Each unit may comprise a single emulsion layer or a plurality of emulsion layers sensitive to a given region of the spectrum. The layers of the element, including the layers of the image-dye-forming units, may be arranged in various orders as known in the art. In an alternative format, the emulsions sensitive to each of the three primary regions of the spectrum may be disposed as a single segmented layer.

A typical multicolor photographic element comprises a support bearing a cyan image-dye-forming unit comprising a red-sensitive silver halide emulsion layer having associated therewith at least one cyan dye-forming coupler; a magenta image-dye-forming unit comprising at least one green-sensitive silver halide emulsion layer having associated therewith at least one magenta dye-forming coupler and a yellow image-dye-forming unit comprising at least one blue-sensitive silver halide emulsion layer having associated therewith at least one yellow dye-forming coupler. The element may contain additional layers, such for example as filter layers, interlayers, overcoat layers and subbing layers.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, England, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1994, item 36544, available as described above, which will be identified hereafter by the term "Research Disclosure". The contents of the Research Disclosure, including the patents and publications referenced therein, are incorporated herein by reference and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through IX. Color materials are described in Sections X through XIII. Scan facilitating is described in Section XIV. Supports, exposure, development systems, and processing methods and agents are described in Sections XV to XX. Certain desirable photographic elements and processing steps are described in Research Disclosure, Item 37038, February 1995.

With negative working silver halide a negative image may be formed. Optionally a positive (or reversal) image may be formed.

The color developing agent may be selected from p-phenylenediamines; typically the agent may be selected from:
4-amino-N, N-diethylaniline hydrochloride,
4-amino-3-methyl-N,N-diethylaniline hydrochloride,
4-amino-3-methyl-N-ethyl-N-(2-methanesulfonamido-ethyl)aniline sesquisulfate hydrate,
4-amino-3-methyl-N-ethyl-N-(2-hydroxyethyl)aniline sulfate,
4-amino-3- (2-methanesulfonamido ethyl) -N,N-diethyl-aniline hydrochloride and
4-amino-N-ethyl-N-(2-methoxyethyl)-m-toluidine di-p-toluene sulfonic acid.

The magenta coupler prepared in accordance with the invention may preferably be used in combination with other classes of image couplers such as 3-acylamino- and 3-anilino-5-pyrazolones and heterocyclic couplers (e.g. pyrazoloazoles) such as, for example, those described in EP 285,274, U.S. Pat. No. 4,540,654 and EP 119,860; and other 5-pyrazolone couplers containing different ballasts or coupling-off groups such as, for example, those described in U.S. Pat. No. 4,301,235, U.S. Pat. No. 4,853,319 and U.S. Pat. No. 4,351,897. Yellow or cyan colored couplers (e.g. to adjust levels of interlayer correction) and/or masking couplers such as, for example, those described in EP 213,490, Japanese Published Application 58-172,647, U.S. Patent 2,983,608, German Application DE 2,706,117C, U.K. Patent No. 1,530,272, Japanese Application A-113935, U.S. Patent 4,070,191 and German Application DE 2,643,965 may also be used. Said masking couplers may be shifted or blocked.

The coupler of the present invention may be used in association with materials that accelerate or otherwise modify the processing steps e.g. of bleaching or fixing to improve the quality of the image. Bleach accelerators described in EP 193,389; EP 301,477; U.S. Pat. No. 4,163,669; U.S. Pat. No. 4,865,956; and U.S. Pat. No. 4,923,784 are particularly useful. Also contemplated is use of the coupler in association with nucleating agents, development accelerators or their precursors (U.K. Patent 2,097,140; U.K. Patent 2,131,188; electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The magenta coupler may be used in combination with filter dye layers comprising colloidal silver sol or yellow and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323). Also, the couplers may in some embodiments be blocked or coated in protected form as described, for example, in Japanese Application 61/258,249 or U.S. Pat. No. 5,019,492.

The invention will now be described with reference to the following example which does not however limit the scope of the invention in any way.

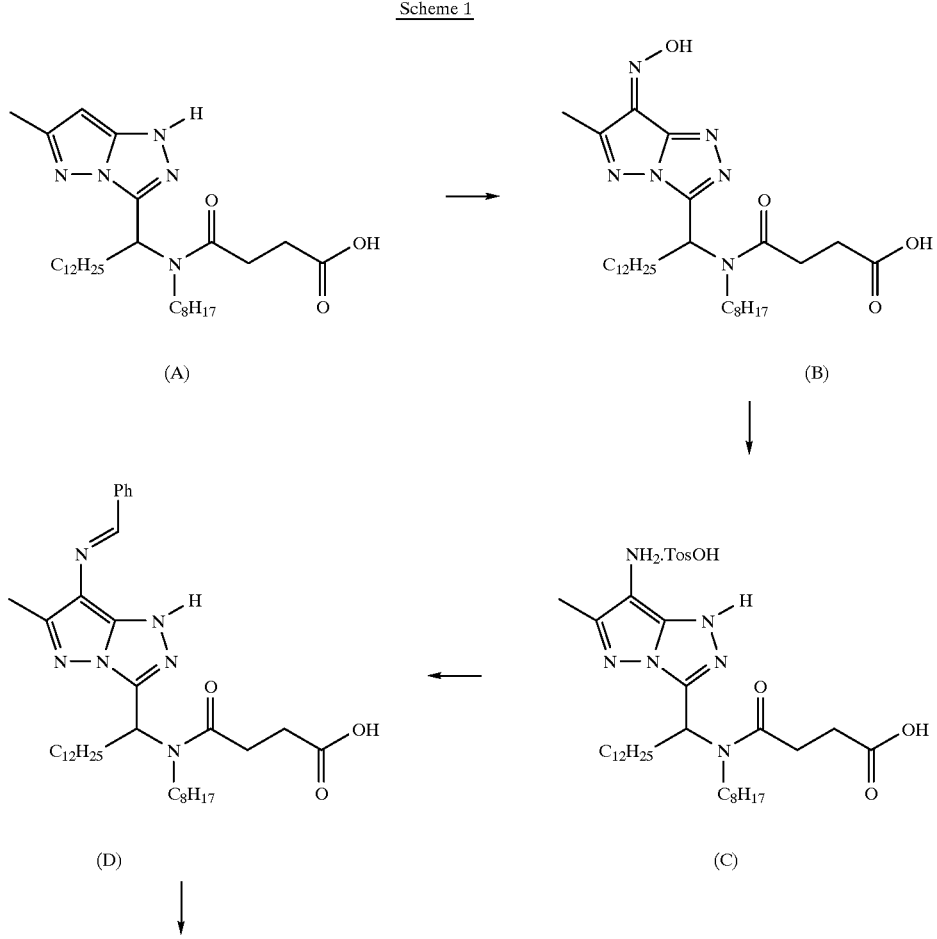

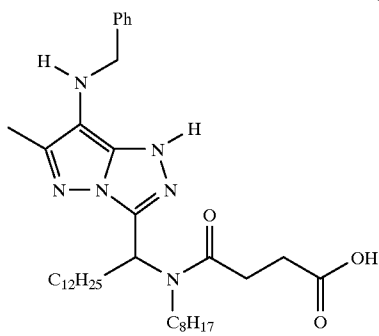

(E)

Preparation of Compound (B)

A solution of compound (A) (13.28 g, 25 mmol) in acetic acid (50 ml) was heated to 60 C on a steam-bath and then removed from the heat. To the stirred solution was added dropwise over ten minutes a solution of sodium nitrite (2.10 g, 30 mmol) in water (6 ml). A solid started to precipitate. The reaction was stirred for 0.5 h then added with stirring to water (1.251). The solid which formed was removed by filtration, washed well with water and dried under vacuum over phosphorus pentoxide. This gave the title compound (B) as a brown foam (13.84 g, 24.7 mmol, 99%).

Preparation of Compound (C)

Tetrahydrofuran (413 ml) and water (32 ml) were added to a mixture of compound (B) (20.48 g, 36.6 mmol), p-toluene-sulphonic acid (6.96 g, 36.6 mmol) and 10% palladium on carbon (1.43 g) under an atmosphere of nitrogen. The suspension was then stirred under hydrogen at one atmosphere pressure for 2 h. The catalyst was removed by filtration through Kieselguhr. The filtrate was dried (magnesium sulphate) and the solvent removed in vacuo. This gave the title compound (C) as an orange-brown foam (26.13 g, 36.34 mmol, 99%).

Preparation of Compound (D)

Benzaldehyde (4.72 g, 44.5 mmol) was added to a stirred solution of compound (C) (31.99, 44.5 mmol) in tetrahydrofuran (180 ml). After 5 minutes triethylamine (4.52 g, 44.8 mmol) was added to the stirred solution and the mixture stirred for 2 h. The solution was added with stirring to water (21) and the solid which formed removed by filtration. This solid was dissolved in ethyl acetate (500 ml). The organic solution was dried (magnesium sulphate) and evaporated in vacuo to give a red solid. This solid was triturated with a hot mixture of methanol (300 ml) and dichloromethane (50 ml) then allowed to cool. The solid was removed and dried under vacuum. This gave the title compound (D) as a pale pink solid (22.20 g, 34.96 mmol, 79%).

Preparation of Compound (E)

A suspension of platinum oxide (0.2 g) in ethanol (200 ml) was stirred under hydrogen at thirty atmospheres pressure for 2 h. Compound (D) (6.35 g, 10.0 mmol) was then added and the reaction stirred for 30 h at 70 C under hydrogen at thirty atmospheres pressure. The reaction was allowed to cool overnight, the catalyst removed by filtration through Kieselguhr and the solvent evaporated in vacuo. This gave the title compound (E) as an orange foam (6.36 g, 10.0 mmol, 100%).

Scheme 2

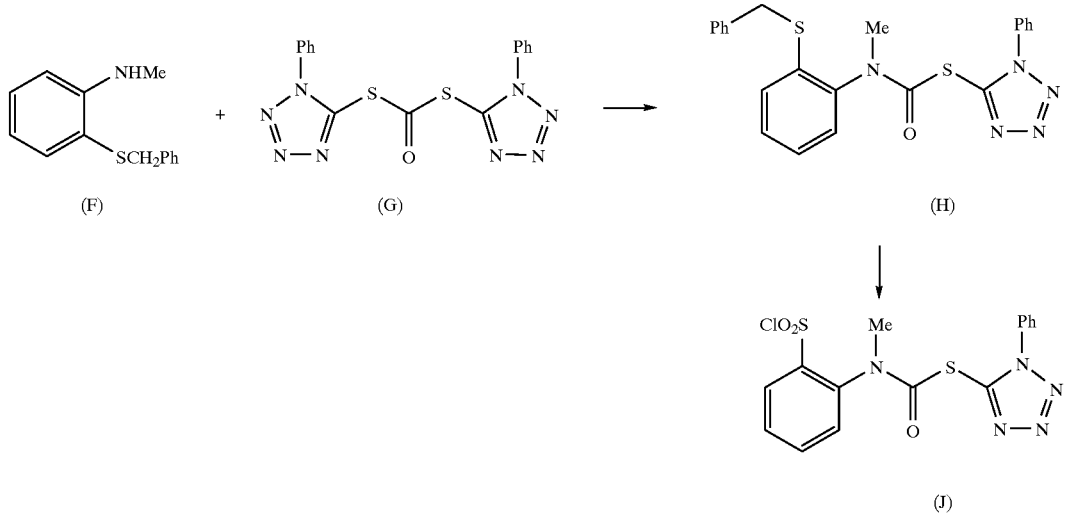

Scheme 3

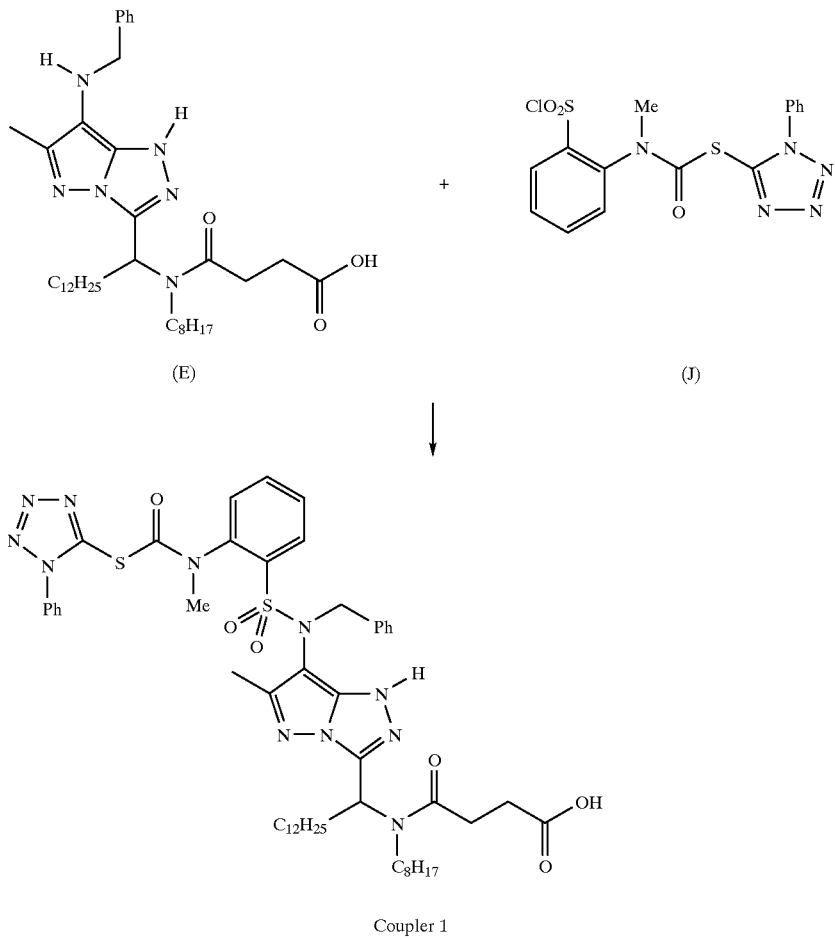

Coupler 1

Preparation of Compound (H)

Compound (G) (CAS Reg No 32276-00-9) (4.25 g, 11.1 mmol) was added to a stirred solution of compound (F) (CAS Reg No 109334-46-5) (2.50 g, 10.9 mmol) in tetrahydrofuran (25 ml). The cloudy solution was stirred for 2 h then added to a mixture of saturated sodium hydrogen carbonate solution (700 ml) and ethyl acetate (200 ml). The organic solution was dried (magnesium sulphate) and concentrated in vacuo to give an oil. This was triturated with ether to give the title compound (H) as a white solid (3.10 g, 7.16 mmol, 66%).

Preparation of Compound (J)

Chlorine gas was bubbled through a stirred suspension of compound (H) (2.88 g, 6.65 mmol) in a mixture of acetic acid (70 ml) and water (7 ml). The temperature rose slowly to 35 C and the solid dissolved. When the temperature had fallen to 25 C the flow of chlorine was replaced by a vigorous flow of nitrogen. After 0.5 h the virtually colorless solution was added with stirring to water (500 ml). After 0.5 h the solid was removed by filtration and dried under vacuum over phosphorus pentoxide. This gave the title compound (J) as a white solid (2.28 g, 5.57 mmol, 84%).

Preparation of Coupler (1)

First compound (J) (9.70 g, 23.7 mmol) then dry pyridine (1.87 g, 23.7 mmol) were added to a stirred solution of compound (E) (15.09 g, 23.7 mmol) in dry tetrahydrofuran (100 ml). The reaction mixture was stirred for 2 h then the solvent was removed in vacuo. The residue was taken up in ethyl acetate (11) and water (11) containing concentrated hydrochloric acid (20 ml). The organic solution was dried (magnesium sulphate) and evaporated in vacuo to give a brown foam. This was purified by column chromatography over silica (eluent 9:1 dichloromethane/methanol) to give coupler (1) as an orange foam (11.36 g, 11.25 mmol, 47%).

PHOTOGRAPHIC EVALUATION OF A MAGENTA DIAR COUPLER

A coupler of the present invention was dispersed in coupler solvent and incorporated, at a range of laydowns, into photographic coatings containing a silver bromoiodide emulsion, on a transparent support, according to the following coating diagram:

| Gel Supercoat | Gelatin | 1.50 g/m$^2$ |
|---|---|---|
| Emulsion | Silver bromoiodide | 0.80 g/m$^2$ |
| Layer | Image Coupler C1 | 1.265 mmol/m$^2$ |
| | Coupler (1) | X mmol/m$^2$ |
| | Gelatin | 2.42 g/m$^2$ |
| | Bis(vinylsulphonyl)-methane (hardener) | 0.06 g/m$^2$ |
| Support | Cellulose acetate | | where X=0, 0.03, 0.06, 0.12 and 0.24 mmol/m$^2$ respectively for Coupler (1).

The image coupler C1 had the following formula:

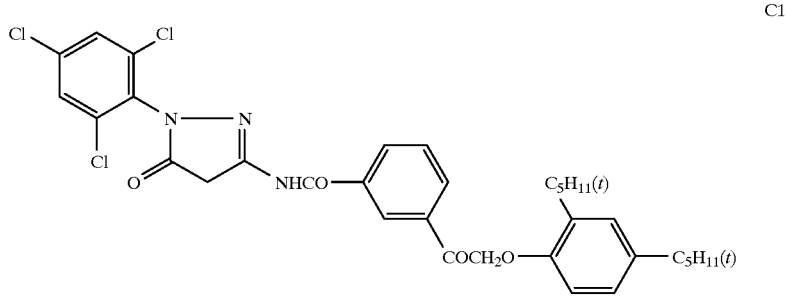

Aqueous dispersions of the couplers were prepared by methods known in the art. The dispersion of Compound (1) used contained 12.5% w/w gelatin, 2.2% w/w coupler and coupler solvents in the ratio:

coupler:tricresyl phosphate:2-(2-butoxyethoxy)-ethyl acetate 1.0:2.0:3.0 (w/w). The auxiliary solvent (2-(2-butoxyethoxy)ethyl acetate) was included to aid in dispersion preparation and was removed by washing the dispersion for 6 hours at 4° C. and pH 6.0.

The dispersion of magenta dye-forming image coupler C1 used contained 6.0% w/w gelatin, 8.8% w/w coupler and coupler solvents in the ratio:

coupler:tricresyl phosphate:2-(2-butoxyethoxy)ethyl acetate 1.0:0.5:1.5 (w/w). The auxiliary solvent (2-(2-butoxyethoxy)ethyl acetate) was included to aid in dispersion preparation and was removed by washing the dispersion for 6 hours at 4üC and pH 6.0.

(i) Sensitometric testing

The experimental photographic coatings prepared in this way were slit and chopped into 30 cm×35 mm test strips.

After hardening the strips were exposed (0.1 sec) through a 0–4.0 neutral density step wedge (0.2 ND step increments) and Daylight V and Wratten 9 filters then processed through a standard C-41 process as described in the British Journal of Photography Annual (1988) 196–198 using the following steps and process times:

| Developer | 2.5 minutes |
|---|---|
| Bleach | 4.0 minutes |
| Wash | 2.0 minutes |
| Fix | 4.0 minutes |
| Wash | 2.0 minutes |

For each test strip, Status M densities were measured as a function of exposure using a spectral array a utomatic transmission densitometer. Measurements of sensitometric parameters—maximum d ensity ($D_{max}$) and contrast ($\gamma$)—were obtained from plots of density vs. log exposure (DlogE curves).

(ii) Investigation of silver develop ment effects

A second set of 35 mm strips was exposed as in (i) for 1.0 sec through a 0–1.8 neutral density step wedge (0.3 ND increments) and Daylight V and Wratten 9 filters. The strips was processed through a modified C-41 process, in which the bleach step was omitted and a stopbath (1% acetic acid solution) was inserted after the developer step, using the following processing sequence:

| Developer | 2.5 minutes |
|---|---|
| Stopbath | 1.0 minute |
| Wash | 2.0 minutes |
| Fix | 4.0 minutes |
| Wash | 2.0 minutes |

The strips processed through the "no bleach" process were subjected to X-ray fluorescence (XRF) analysis to determine the amount of developed silver in each of the seven steps of the processed strip. Silver development curves (developed silver in mg/m² vs. step number (or log exposure)) were then created. Visual inspection of the silver development curves was used to assess any silver inhibition effects promoted by the compounds of the invention.

In the Table below the reduction in maximum density ($D_{max}$) obtained by mixing varying quantities of Coupler (1) with a fixed amount of the image coupler C1 is shown.

TABLE

| IMAGE COUPLER | LAYDOWN OF (1) mmol/m² | $D_{max}$ | Loss in $D_{max}$ % |
|---|---|---|---|
| C1 | 0.00 | 2.24 | 0 |
| C1 | 0.03 | 2.18 | 3 |
| C1 | 0.06 | 2.16 | 4 |
| C1 | 0.12 | 1.95 | 13 |
| C1 | 0.24 | 1.68 | 25 |

It will be seen that Coupler (1) is effective at controlling the maximum density at reasonable laydown levels.

The invention has been described in detail with particular reference to preferred embodiments thereof, but it will be understood that variations and modifications can be effected within the spirit and scope of the invention.

What is claimed is:

1. A photographic element containing an image dye-forming coupler, in association with a light-sensitive silver halide emulsion layer wherein the coupler has the formula (I)

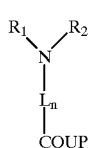

(I)

wherein L is an oxymethylene or oxycarbonyl group; n is 0 or 1; COUP is a coupler moiety and $R_1$ and $R_2$ are the same or different and are groups selected such that (a) together with the nitrogen atom a good leaving group is formed;

(b) at least one of them contains a PUG linked to an electrophilic centre (E);

(c) said nitrogen atom is spatially related with regard to said electrophilic centre to allow intramolecular reaction to release the PUG; and (d) neither $R_1$ nor $R_2$ is a hydrogen atom.

2. An element containing a coupler of formula (I) according to claim 1 wherein $R_1$ and $R_2$ are groups selected from alkyl, aryl, alkenyl, aralkyl, heterocyclyl; alkyl-, aryl- or heterocyclylsulfonyl; alkyl- or arylcarbonyl; alkyl- or arylthiocarbonyl; alkyl- or aryloxycarbonyl; alkyl- or arylthioalkoxycarbonyl; carbamoyl, thiocarbamoyl, imino or haloalkyl, each of which may be unsubstituted or substituted with any group that does not adversely affect the nature of the timing group or E, or $R_1$ and $R_2$ may, together with the nitrogen atom, form a 5–10 membered heterocyclic ring system which may contain one or more further heteroatoms selected from N, O and S, said ring being unsubstituted or substituted.

3. An element containing a coupler of formula (I) according to claim 2 wherein $R_1$ and $R_2$ are different and at least one is selected from unsubstituted or substituted alkyl-, aryl- or heteroarylsulfonyl; aryl or heteroaryl; and alkyl- and arylcarbonyl.

4. An element containing a coupler of formula (I) according to claim 3 wherein at least one of $R_1$ and $R_2$ is unsubstituted or substituted arylsulfonyl.

5. An element containing a coupler of formula (I) according to claim 1 wherein n is 0.

6. An element containing a coupler of formula (I) according to claim 1 wherein E is selected from unsubstituted or substituted primary, secondary or tertiary alkyl; alkyl- or arylcarbonyl; alkyl- or arylimino; thiocarbonyl; alkyl- or aryloxycarbonyl; alkyl- or arylthioalkoxycarbonyl; carbamoyl, thiocarbamoyl, alkenyl, phosphinyl and thiophosphinyl.

7. An element containing a coupler of formula (I) according to claim 6 wherein E is selected from unsubstituted or substituted primary or secondary alkyl; alkyl- or arylcarbonyl; arylimino; alkyl- or aryloxycarbonyl and carbamoyl.

8. An element containing a coupler of formula (I) according to claim 7 wherein E is unsubstituted or substituted carbamoyl.

9. An element containing a coupler of formula (I) according to claim 1 wherein the PUG is selected from oxazoles, thiazoles, diazoles, triazoles, oxadiazoles, thiadiazoles, oxathiazoles, thiatriazoles, benzo-triazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercapto benzimidazoles, selenobenzimidazoles, benzodiazoles, mercaptooxazoles, mercaptothiadiazoles, mercaptothiazoles, mercaptotriazoles, mercaptothiatriazoles, mercaptooxadiazoles, mercaptodiazoles, mercaptooxathiazoles, tellurotetrazoles, benzisodiazoles and mercaptopropionic acid.

10. An element containing a coupler of formula (I) according to claim 1 which is a magenta image dye-forming coupler.

11. An element containing a coupler of formula (I) according to claim 1 having the formula

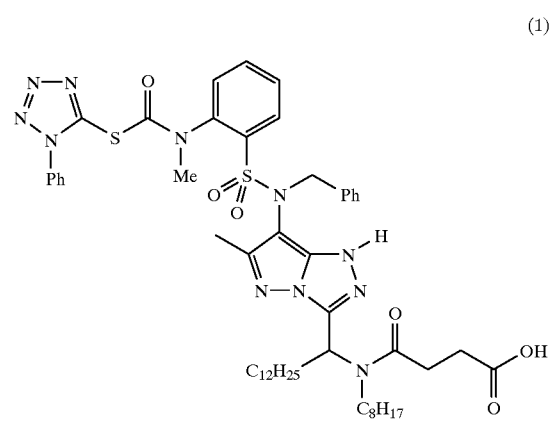

(1)

12. A multi-colour photographic material comprising a support bearing yellow, magenta and cyan image dye-forming units comprising at least one blue-, green- or red-sensitive silver halide emulsion layer having associated therewith at least one yellow, magenta or cyan dye-forming coupler respectively, wherein at least one image dye-forming coupler is a coupler of formula (I)

(I)

wherein L is an oxymethylene or oxycarbonyl group; n is 0 or 1; COUP is a coupler moiety and $R_1$ and $R_2$ are the same or different and are groups selected such that (a) together with the nitrogen atom a good leaving group is formed;

(b) at least one of them contains a PUG linked to an electrophilic centre (E);

(c) said nitrogen atom is spatially related with regard to said electrophilic centre to allow intramolecular reaction to release the PUG; and (d) neither $R_1$ nor $R_2$ is a hydrogen atom.

* * * * *